United States Patent
Maminishkis

(10) Patent No.: US 10,729,579 B2
(45) Date of Patent: Aug. 4, 2020

(54) SURGICAL TOOL AND METHOD FOR OCULAR TISSUE TRANSPLANTATION

(71) Applicant: THE UNITED STATES OF AMERICA, AS REPRESENTED BY THE SECRETARY, DEPARTMENT OF HEALTH & HUMAN SERVICES, Rockville, MD (US)

(72) Inventor: Arvydas Maminishkis, Bethesda, MD (US)

(73) Assignee: National Institutes of Health, Rockville, MD (US)

( * ) Notice: Subject to any disclaimer, the term of this patent is extended or adjusted under 35 U.S.C. 154(b) by 126 days.

(21) Appl. No.: 15/325,584

(22) PCT Filed: Jul. 10, 2015

(86) PCT No.: PCT/US2015/039932
§ 371 (c)(1),
(2) Date: Jan. 11, 2017

(87) PCT Pub. No.: WO2016/007852
PCT Pub. Date: Jan. 14, 2016

(65) Prior Publication Data
US 2017/0128263 A1    May 11, 2017

Related U.S. Application Data

(60) Provisional application No. 62/023,289, filed on Jul. 11, 2014.

(51) Int. Cl.
*A61F 9/00*    (2006.01)

(52) U.S. Cl.
CPC .......... *A61F 9/0026* (2013.01); *A61F 9/0008* (2013.01)

(58) Field of Classification Search
CPC ..... A61F 9/0026; A61F 9/0008; A61F 9/0017
See application file for complete search history.

(56) References Cited

U.S. PATENT DOCUMENTS

| 5,868,728 A |   | 2/1999 | Giungo et al. |
|---|---|---|---|
| 6,159,218 A | * | 12/2000 | Aramant ............. A61F 9/00727 128/897 |
| 6,579,256 B2 | * | 6/2003 | Hughes ..................... A61F 2/14 600/7 |

(Continued)

FOREIGN PATENT DOCUMENTS

| JP | 2005517468 A | 6/2005 |
|---|---|---|
| JP | 2010533565 A | 10/2010 |

(Continued)

OTHER PUBLICATIONS

International Search Report for PCT Application No. PCT/2015/039932, dated Sep. 22, 2015.

(Continued)

*Primary Examiner* — Diane D Yabut
(74) *Attorney, Agent, or Firm* — Locke Lord LLP; Christopher J. Capelli; Nicholas J. DiCeglie, Jr.

(57) ABSTRACT

Described are devices and methods for delivering a sheet of tissue into the eye in such a way that damage to the tissue is minimized, damage to the eye during insertion and manipulation of the tissue is minimized, and the tissue is released and delivered in a precise and controlled fashion.

17 Claims, 12 Drawing Sheets

(56) References Cited

U.S. PATENT DOCUMENTS

| | | | |
|---|---|---|---|
| 9,808,372 B2* | 11/2017 | Inoue | A61F 9/0017 |
| 2004/0185083 A1 | 9/2004 | Dionne et al. | |
| 2008/0281341 A1 | 11/2008 | Miller et al. | |
| 2013/0178822 A1 | 7/2013 | Hickingbotham et al. | |
| 2013/0296254 A1 | 11/2013 | Deschatelets et al. | |
| 2014/0287061 A1* | 9/2014 | Landolina | A61L 24/001 |
| | | | 424/617 |

FOREIGN PATENT DOCUMENTS

| | | |
|---|---|---|
| WO | WO-201214946 A1 | 2/2012 |
| WO | WO-2012018006 A1 | 2/2012 |

OTHER PUBLICATIONS

First Office Action from the Japanese Patent Office for Japanese Patent No. JP2017501212, dated Apr. 16, 2019.

* cited by examiner

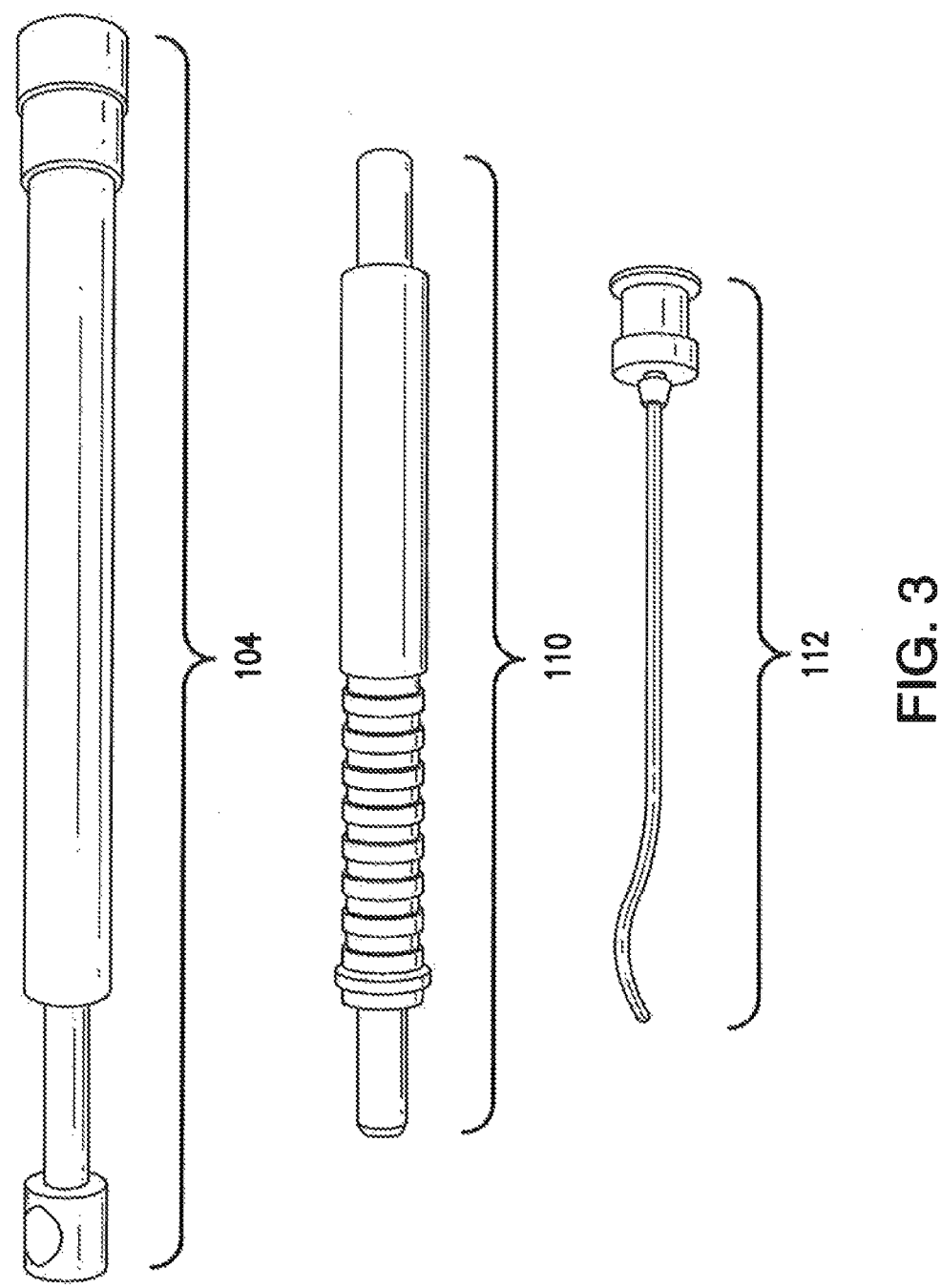

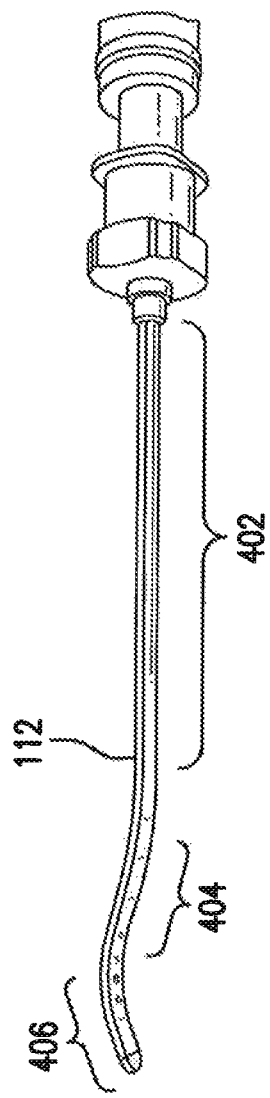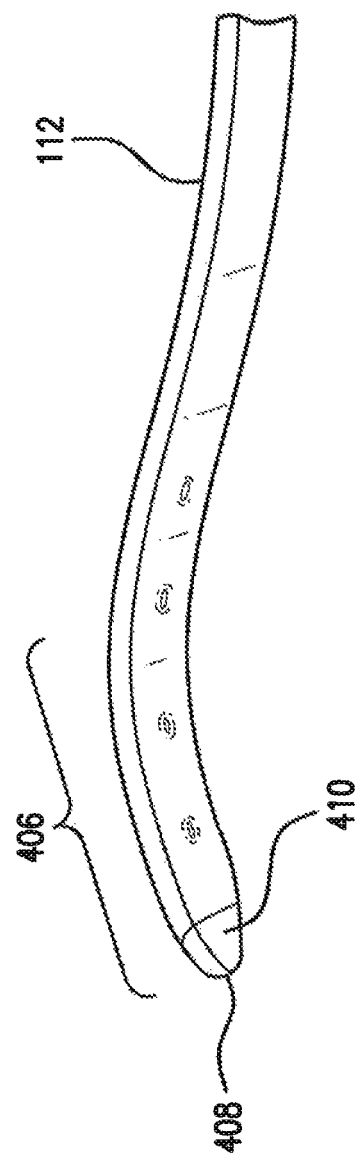

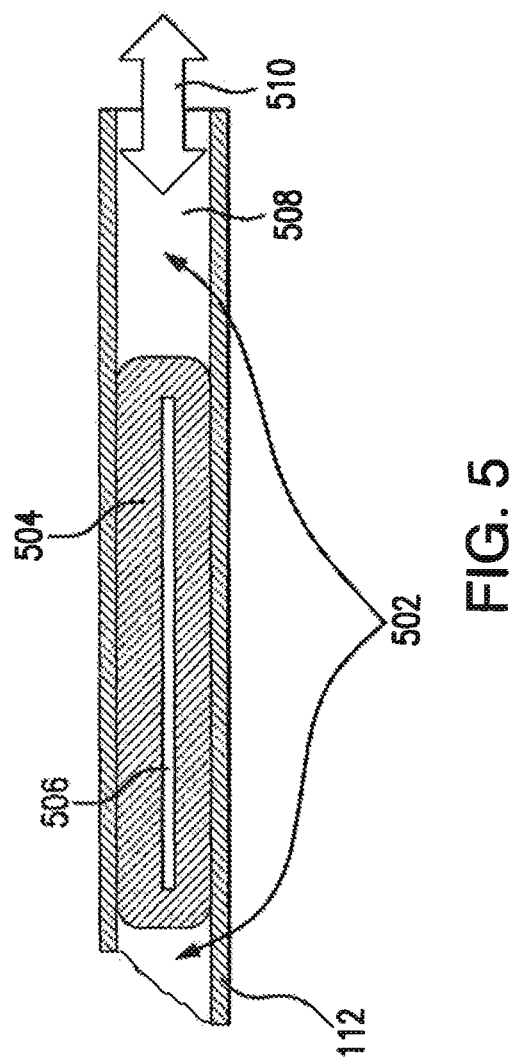

SURGICAL TOOL AND METHOD FOR OCULAR TISSUE TRANSPLANTATION

CROSS REFERENCE TO RELATED APPLICATIONS

This application is a national stage application of PCT application PCT/US2015/039932 filed Jul. 10, 2015, which claims the benefit of U.S. Provisional Patent Application Ser. No. 62/023,289 filed Jul. 11, 2014, which are expressly incorporated by reference herein.

GOVERNMENT SUPPORT

This invention was funded by the National Institutes of Health. The United States Government has certain rights in this invention.

FIELD OF INVENTION

The present invention generally relates to a device and technique for use in ocular procedures, and more particularly to a device and technique for holding and precisely delivering a small piece of tissue or cells into the subretinal space (SRS) while protecting the piece of tissue or cells from damage during the procedure.

BACKGROUND OF THE INVENTION

Many ocular procedures involve the insertion of materials into the eye, including fluids, tissues, cells and grafts. During such procedures, one key requirement is the insertion of the various materials through as small an incision as possible to minimize trauma to the eye. Further, due to the delicate nature of many of the materials that are inserted, it is important that the devices and techniques adequately protect the materials during manipulation and insertion. In addition, in light of the need for minimal manipulation of the device within the eye to prevent trauma to the eye, it is important that the device and technique enables precise and controlled insertion at a desired target location within the eye so as to minimize the need for post-insertion repositioning of the material inserted.

Endothelial keratoplasty (EK) is one type of procedure that involves the insertion of tissue into the eye. In particular, EK involves selectively replacing the diseased layer of the cornea and leaving healthy areas intact. During the EK procedure, the diseased inner cell layer of the cornea is removed, and healthy donor tissue is implanted through a small incision. One common method that surgeons have used for inserting tissues within the eye involves the use of forceps to grasp and fold/roll the delicate tissue, followed by inserting the forceps with the grasped tissue into the eye. However, this technique and device cannot be used in a subretinal space and could cause significant trauma to the very delicate retina tissue.

A variety of devices and techniques have been developed that somewhat reduce such eye trauma and tissue damage during insertion of materials into the eye.

For example, U.S. Patent Application Publication No. 2013/0085567 to Tan et al. describes a device and technique that aids in the manipulation of the thin DM/endothelial complex, so as to greatly simplify the donor handling, and AC manipulation stages, of DMEK surgery. The device houses a donor tissue in a coiled configuration within a chamber for transplantation into the eye. The donor tissue is then placed at a desired location within the eye by grasping the donor tissue with forceps which are inserted through a second incision in the eye and pulling the donor tissue out of the chamber into the eye.

U.S. Pat. No. 8,029,515 to Shiuey describes a device and technique for delivering a corneal implant, particularly through a corneal incision that is substantially less than the width of the implant such that the implant is placed within or between any of the layers of the cornea including the epithelium, Bowman's membrane, stroma, Descemet's membrane, and endothelium. The device includes a hollow member that constrains the corneal implant, and an implant mover or axial pusher that is used to engage and push the implant through and out of the hollow member into the corneal pocket.

Thus, while devices and techniques have been developed that somewhat reduce such eye trauma and tissue damage during insertion of materials into the eye, further improvements are still needed to address retina damage issue and placing implant into very limited in space-subretinal compartment. In addition, there is a need for devices and techniques that provide for more precise and controlled delivery of the tissues into the eye.

SUMMARY OF THE INVENTION

The present invention features devices and techniques that can deliver a sheet of tissue into the eye in such a way that damage to the tissue is minimized, damage to the eye during insertion and manipulation of the tissue is minimized, and the tissue is released and delivered in a precise and controlled fashion.

According to one aspect, a device for performing tissue transplantation within an eye is disclosed. The device includes a hollow handle portion configured to convey a fluid therein. The device also includes an injector portion fluidically coupled to the handle portion and defining an internal channel via which the fluid is conveyed. The injector portion includes a substantially flat tip that defines an aperture connected to the internal channel of the injector portion and configured to enshroud a tissue for transplantation. When a vacuum pressure is applied to the tissue via the fluid, the tissue is held in place within the tip aperture. When an injection pressure that is opposite in direction to the vacuum pressure is applied to the tissue via the fluid, the tissue is injected into the eye.

Embodiments in accordance with this aspect of the invention can include the following features. The device may also include a syringe configured to house a reservoir of the fluid. The syringe may be fluidically coupled to the handle portion to convey the fluid between the syringe and the handle portion. The device may further include a syringe pump coupled to the syringe and configured to regulate the vacuum and insertion pressures. In some cases, the syringe pump is electronically controlled. In one embodiment, the tip of the injector portion is tapered. The injector portion may also include an elongated portion that defines a longitudinal axis and a middle portion that curves away from the longitudinal axis of the elongated portion, wherein the tip of the injector extends from the middle portion and curves towards the longitudinal axis. In some cases, the handle portion and the injector portion are removably coupled. The fluid conveyed within the injector portion of the device may be a liquid alginate or a hyaluronic acid solution, in various embodiments. The tissue may also be coated in a cured alginate.

According to another aspect, the present invention features a method of transplanting tissue into an eye. The method includes vacuuming a sheet of tissue into an aperture of a tip of a surgical injector tool, with the aperture providing a suction force to the sheet of tissue via a fluid. The method also includes inserting the tip of the injector tool into an implantation area of the eye. The method further includes injecting the sheet of tissue into the implantation area by providing an injection force to the sheet of tissue, via the fluid, that is opposite to the suction force.

Embodiments in accordance with this aspect of the invention can include the following features. The method may further include cutting the sheet into a desired shape for implantation and coating the cut sheet of tissue with a biodegradable material. In some cases, the biodegradable material is an alginate material cured using a calcium chloride mist. The fluid may be a liquid alginate or a hyaluronic acid solution. The tip of the surgical injector tool may be substantially flat and the surgical injector tool may be curved in a direction extending distally away from a handle of the surgical injector tool. In some cases, the method also includes using a syringe to regulate the fluid such that the suction and injection forces are applied to the sheet of tissue.

According to a further aspect, a system for performing tissue transplantation within an eye is disclosed. The system includes means for hydraulically securing a sheet of tissue to be implanted and means for injecting the secured sheet of tissue into a transplantation area of the eye. In some embodiments, the system also includes means for positioning the sheet of tissue for injection into the transplantation area of the eye.

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated in and constitute a part of this specification, illustrate several embodiments of the invention and, together with the description, serve to explain the principles of the invention.

Definitions

To facilitate an understanding of the present invention, a number of terms and phrases are defined below.

As used herein, the singular forms "a", "an", and "the" include plural forms unless the context clearly dictates otherwise. Thus, for example, reference to "a sensor" includes reference to more than one sensor.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "reduces" is meant a negative alteration of at least 5%, 10%, 25%, 50%, 75%, or 100%.

By "increases" and is meant a positive alteration of at least 5% 10%, 25%, 50%, 75%, or 100%.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the terms "treat," treating," "treatment," and the like refer to reducing or ameliorating a disease or condition, e.g., leukemia, and/or symptoms associated therewith. It will be appreciated that, although not precluded, treating a disease or condition does not require that the disease, condition, or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "alginate" refers to alginic acid, or compounds or solutions thereof.

Any compounds, compositions, apparatus, or methods provided herein can be combined with one or more of any of the other compounds, compositions, apparatus, and methods provided herein.

DESCRIPTION OF THE DRAWINGS

FIG. 3 illustrates the components of the surgical tool shown in FIGS. 1-2 in greater detail;

FIGS. 4A-4B illustrate the injector of the surgical tool of FIGS. 1-3 in greater detail;

FIG. 5 illustrates a cross-sectional view of the injector of FIGS. 4A-4B;

DETAILED DESCRIPTION OF THE INVENTION

The present invention generally relates to a device and method for use in ocular procedures, particularly retinal surgeries, wherein the device holds a small piece of tissue or cells and allows for the delivery of the piece of tissue or cells into the eye, particularly the subretinal space (SRS), in a desired orientation while protecting the piece of tissue or cells from damage during the procedure. The device and method further provides for the delivery of the piece of tissue or cells into the eye while minimizing trauma to the eye. Notably, the presence of a scaffold in the SRS may make it more difficult for a wound to heal. In addition, such a scaffold may also impair oxygen and nutrient access by implanted retinal pigment epithelium (RPE) cells during a procedure.

Figure 1:
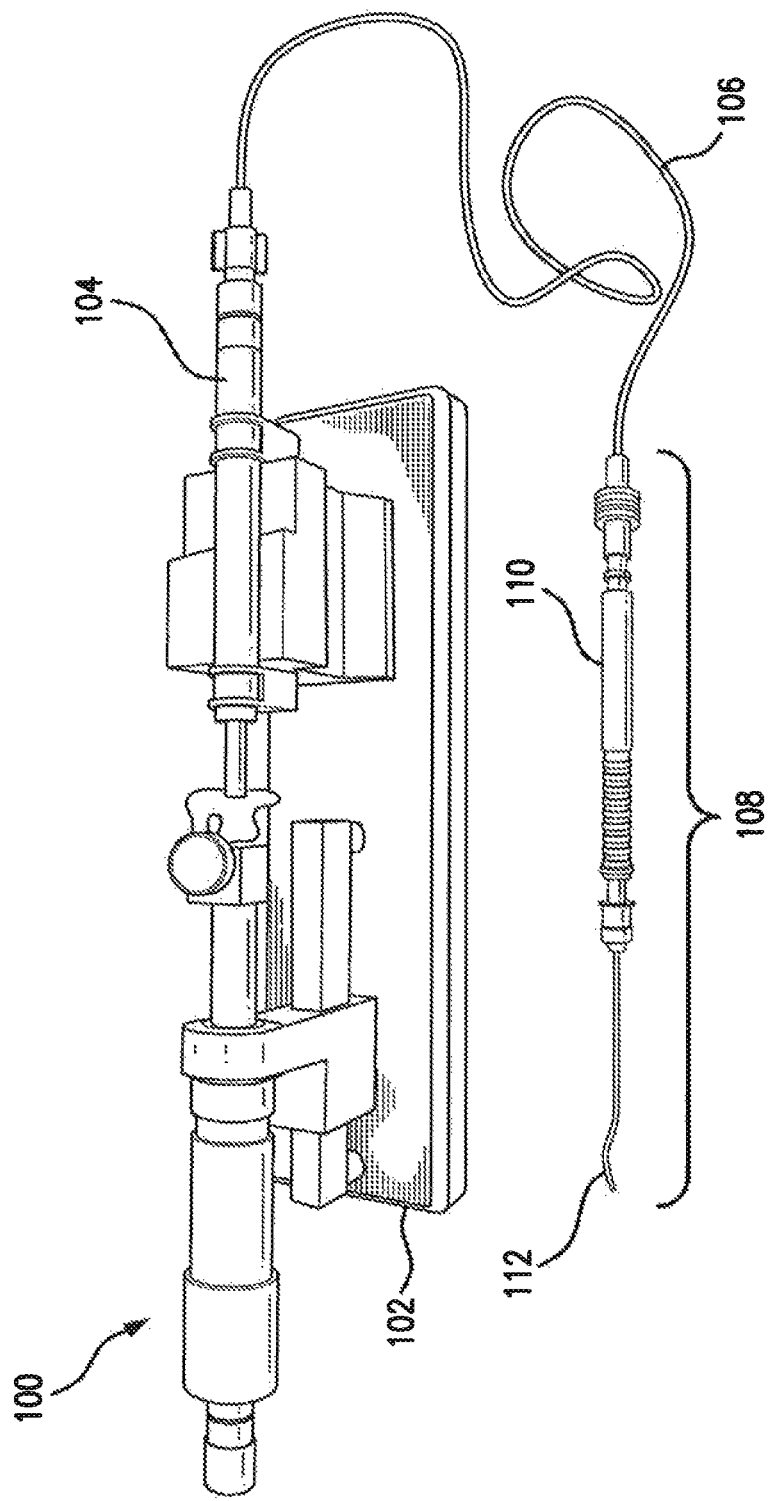
FIG. 1 illustrates a system for performing soft tissue transplantation.
Figure 2:
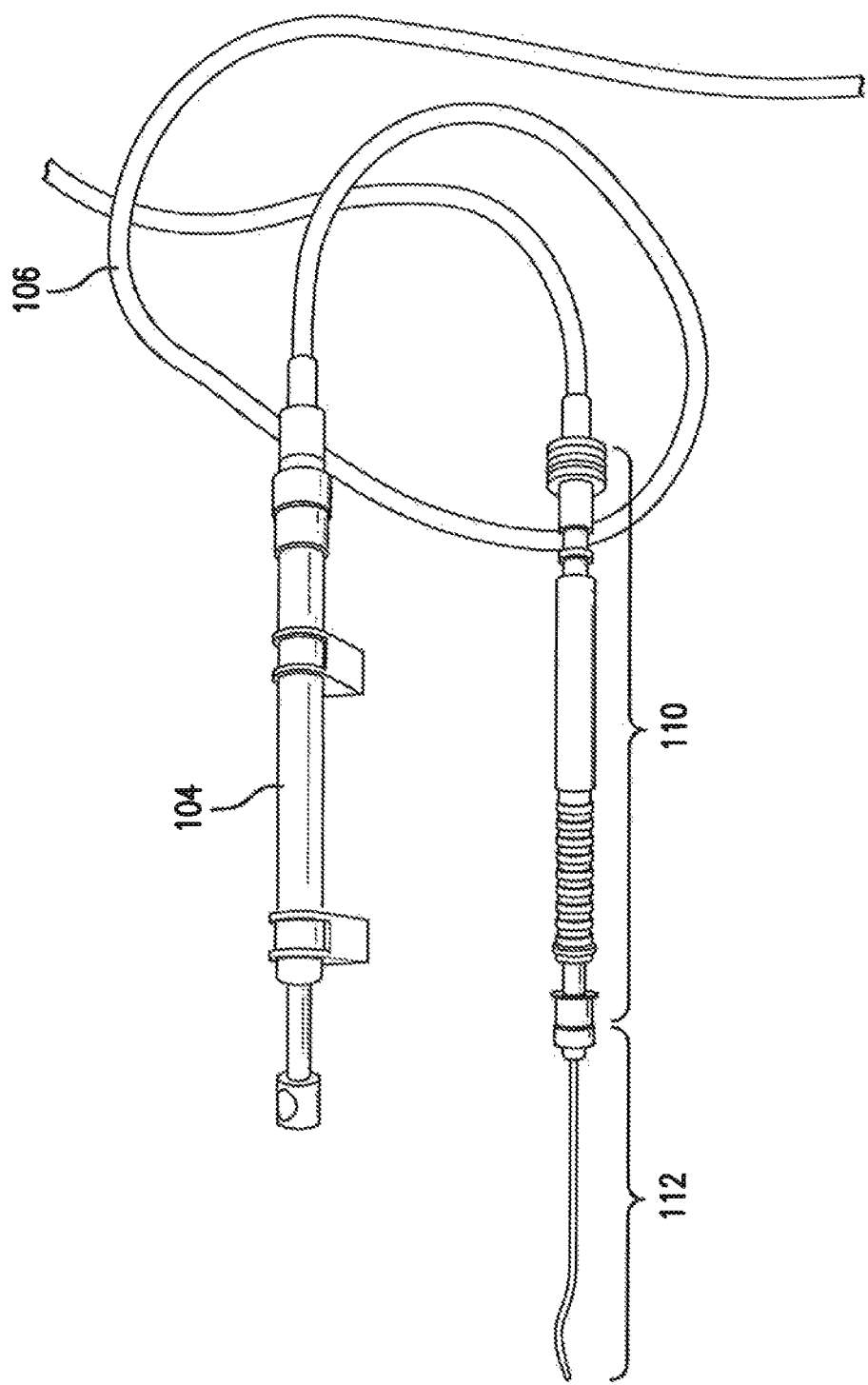
FIG. 2 illustrates the components of the system of FIG. 1 in greater detail.

Referring now to FIGS. 1-3, a system 100 for performing soft tissue transplantation is shown, according to various embodiments. Advantageously, system 100 may be able to support the implantation of monolayer RPE cultures while minimizing the presence of a scaffold (e.g., 200 µm for a rigid scaffold vs 5 µm for a soft scaffold) within the transplantation area.

Figure 13:
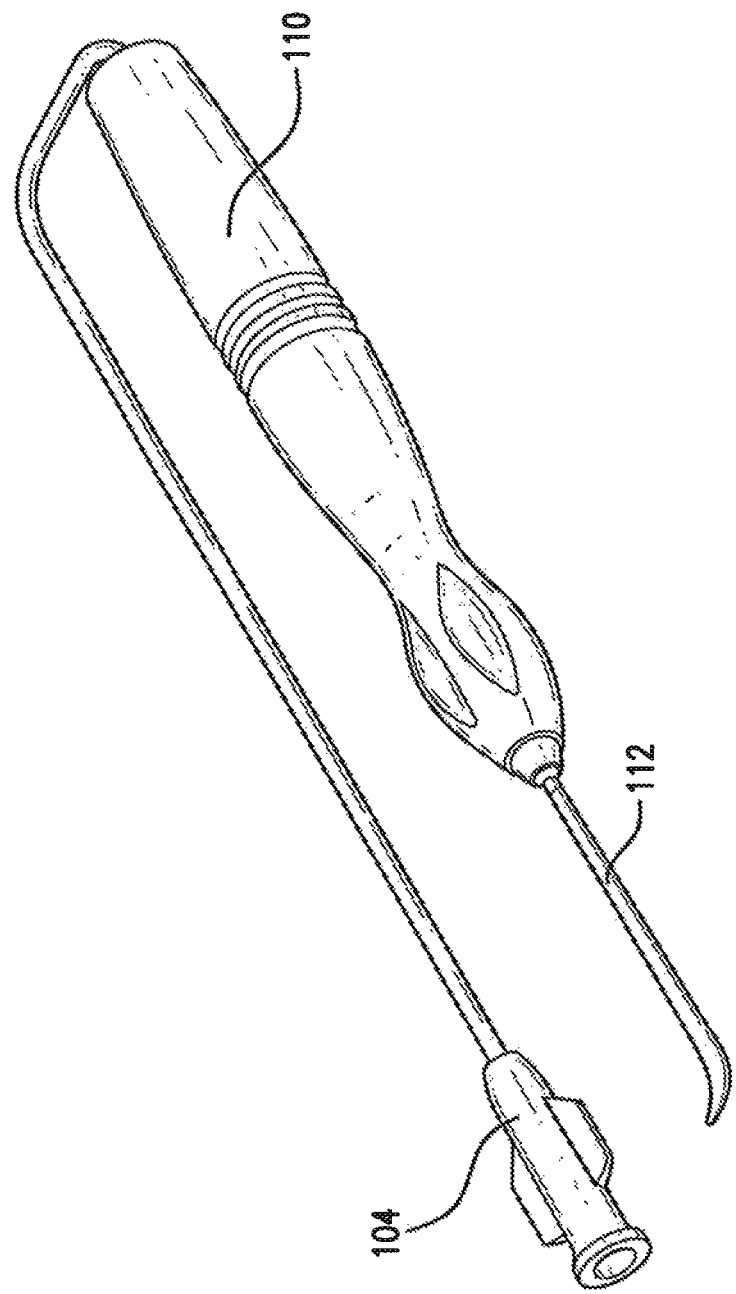
FIG. 13 illustrates another embodiment of the surgical tool of FIGS. 1-3 showing an ergonomically shaped handle portion.

As shown, system 100 may include a surgical tool 108 that includes a handle portion 110 and an injector portion 112. Surgical tool 108 may be formed using any material suitable for performing a medical procedure such as, but not limited to, stainless steel, titanium, carbon fiber, polymers, plastic or the like. In various embodiments, both handle portion 110 and injector portion 112 are hollow structures that form a channel that extends substantially through each of portions 110, 112 and are fluidically coupled. In one embodiment, injector portion 112 and handle portion 110 may be removably coupled. For example, as shown in FIG. 3, handle portion 110 and injector portion 112 may be coupled via a screw mechanism whereby injector portion 112 screws onto handle portion 110. In other implementations, other coupling mechanisms may be used to couple injector portion 112 to handle portion 110 (e.g., a hook-and-latch mechanism, a locking ball, a locking mechanism actuated by a button located on handle portion 110, etc.). Notably, removably coupling injector portion 112 to handle portion 110 may facilitate injector portion 112 being used in a disposable or recyclable manner after the procedure is complete. Referring to FIG. 13, an alternate embodiment of tool 108 is shown. In this embodiment, the handle portion 110 includes an hourglass shape with ridges for hand and finger placement which is more ergonomic to facilitate comfort for the surgeon and operation precision. Portions 112, 110, and 106 can be permanently bound to plastic handle producing a disposable single use instrument.

Also as shown, system 100 may include a syringe 104 configured to house a reservoir of a fluid. Syringe 104 may be fluidically coupled to the internal channel of handle portion 110 by a tube 106, thereby allowing the fluid to be conveyed into and out of surgical tool 108. Any suitable connection mechanism may be used to couple extension tube 106 to surgical tool 108 and syringe 104 such as, but not limited to, slip fittings, screw-on fittings, etc.

In some embodiments, system 100 may further include a syringe pump 102 that actuates syringe 104, thereby regulating the fluidic pressure within surgical tool 108. As shown in FIG. 1, syringe pump 102 may be configured to be operated manually and provide stability to syringe 104. In other embodiments, syringe pump 102 may be hand-held and/or electronically controlled, to regulate the amount of fluid pressure within system 100. Other vacuum/pressure producing systems can be also used to control syringe plunger. Vitreoretinal Surgery Systems (E.g. ACCURUS, Constelation, or the like) have a VFC system which can directly be connected or through the use of an adapter, for example, adapter manufactured by MedOne Surgical (headquartered in Sarasota, Fla.) can be used to connect to syringe and regulate the fluidic pressure within surgical tool 108.

Figure 10:
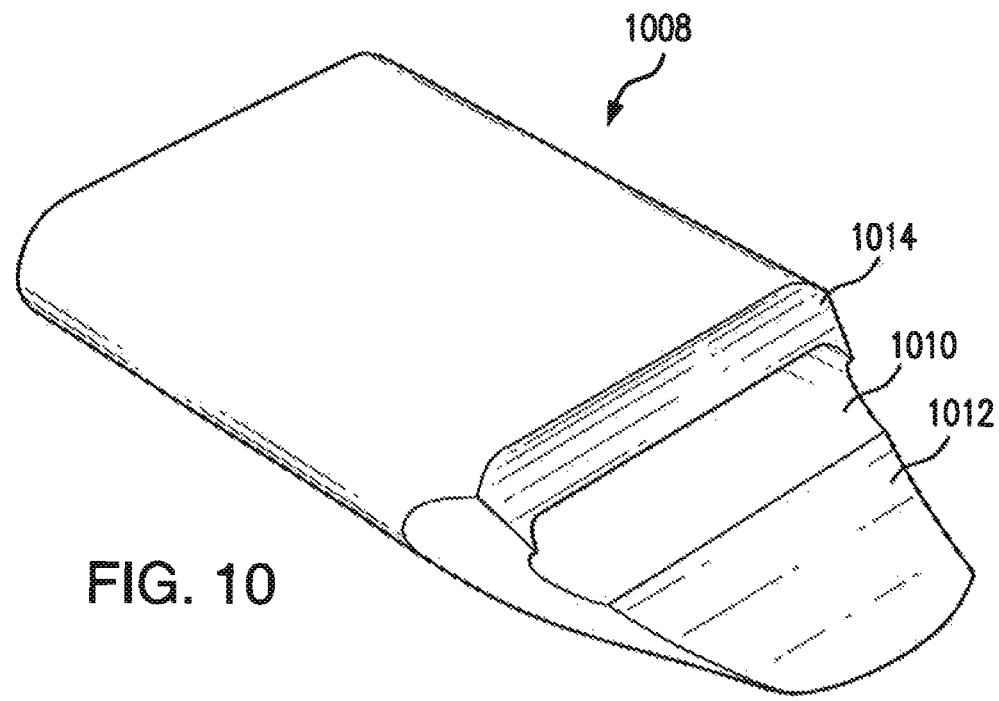
FIG. 10 illustrates an embodiment of a tip of the injector of FIGS. 4A-4B having a tapered angled edge.
Figure 11:
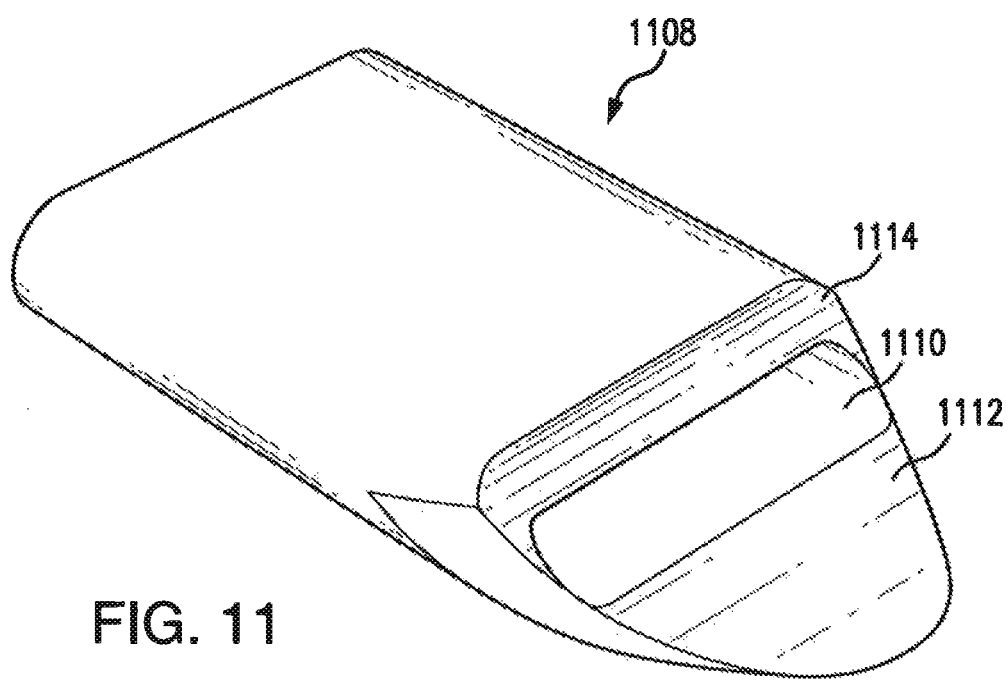
FIG. 11 illustrates an embodiment of a tip of the injector of FIGS. 4A-4B having a tapered rounded edge.
Figure 12:
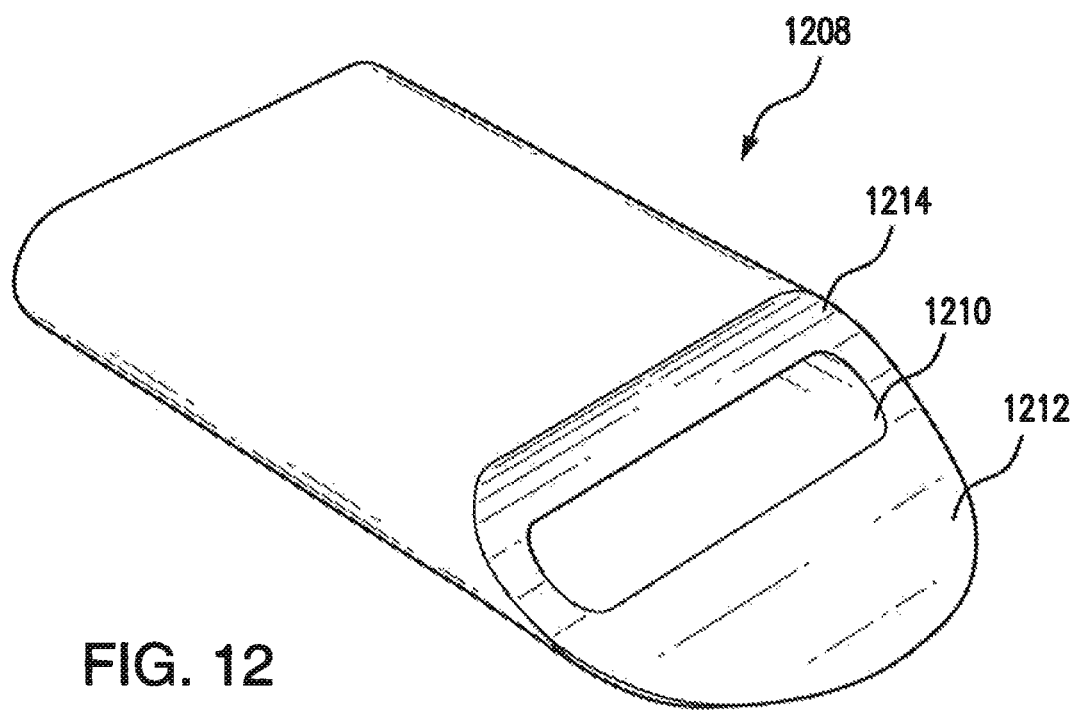
FIG. 12 illustrates an embodiment of a tip of the injector of FIGS. 4A-4B having a semi-circular edge.

Referring now to FIGS. 4A-4B, injector portion 112 of surgical tool 108 is shown in greater detail, according to various embodiments. As shown, injector portion 112 may include an elongated portion 402 that extends from handle portion 110 substantially along the same longitudinal axis as handle portion 110 when coupled to handle portion 110. Injector portion 112 may also include a middle portion 406 that curves away from the longitudinal axis of elongated portion 402 and a tip 408 that curves back towards the longitudinal axis defined by elongated portion 402. Said differently, injector portion 112 may be of S-shape or flattened S-shape, thereby allowing tip 408 to be inserted into the transplant area at an angle that is substantially less than perpendicular to the eye. Notably, the reduced angle of insertion afforded by the curvature of injector portion 112 may reduce the change of damaging Bruch's membrane within the eye and causing unwelcomed bleeding during the procedure. As shown in greater detail in FIGS. 4B and 10-12, tip 408, 1008, 1108 and 1208 of injector portion 112 may also be substantially flat and may be tapered or otherwise pointed at its distal end, to facilitate insertion of tip 408, 1008, 1108 and 1208 into the transplant area of the eye. According to various embodiments, an aperture 410, 1010, 1110, and 1210 may be formed between an upper and lower portion of tip 408, 1008, 1108 and 1208. Aperture 410, 1010, 1110, and 1210 may be fluidically connected to the internal channel of injector portion 112 and configured to enshroud the tissue to be transplanted. With continued reference to FIGS. 10-12 various embodiments of tip 1008, 1108 and 1208 are shown. Tips 1008, 1108 and 1208 vary in the shape of the lower portion 1012, 1112, 1212 which extends past the upper portion 1014, 1114, 1214. The lower portion 1012, 1112, 1212 can include a tapered angled edge, as shown with tip 1008, tapered rounded edge, as shown with tip 1108, or semi-circular edge, as shown with tip 1208, to facilitate insertion. Tip 408, 1008, 1108 and 1208 may be made of the same material as the injector portion and handle portion or the tip 408, 1008, 1108 and 1208 may be made of plastic, such as fluorinated ethylene propylene (FEP). Plastic provides hydrophobic properties including preventing the tissue to be transplanted from sticking to the tip and allowing easier discharge of the implant from the instrument.

Injector portion 112 may be constructed in any number of ways. For example, injector portion 112 may be formed from a needle of any suitable size (e.g., 18 gauge, 19 gauge, 20 gauge, etc.). Such a needle may be polished, shaped to form the wedge of tip 408, and bent to form a curvature similar to the one shown. In other cases, injector portion 112 may be constructed wholly or partially on its own using castings, milling, or other suitable construction techniques or by plastic molding and machining.

FIG. 5 illustrates a cross-sectional view of the injector portion 112 of surgical tool 108 during operation, according to various embodiments. As shown, a layer of tissue 506, such as a monolayer RPE culture, may be hydraulically held in place within injector portion 112 until positioned for injection into the transplant area of the eye. In some embodiments, the system 100 may include an implant loading platform for facilitating placement of the layer of tissue 506. The implant loading platform can include, for example, a molded silicone pad with a channel and an additional liquid reservoir to quickly position implant into the correct direction for loading. The channel width corresponds to a width of the implant tool tip when the implant tool tip is placed in this channel. The channel provides a guided path for the implant to follow until it reaches the tool tip. Silicon allows for flexibility and less damage to the tool tip if the tip is moved or twisted during loading procedure. The channel and reservoir can be filled with any desired loading solution. Those skilled in the art will recognize that the implant loading pad is not limited to placement of implant tissue but can also be used for quicker positioning/loading of implants or surgical tools as needed for the surgical procedure. A fluid 502 located within the internal channel 508 of injector portion provides vacuum or injection pressures 510 to tissue 506, based on actuation of syringe 104. For example, tissue 506 may be vacuumed into aperture 410 and held in place within channel 508 by drawing syringe 104. A clamp may be used to introduce the tool and eliminate complication related to loss of eye pressure. After positioning tip 408 within the transplant area, depressing syringe 104 causes fluid 502 to apply an injection pressure to tissue 506 in the opposite direction of the vacuum pressure, thereby forcing tissue 506 through aperture 410 and into the transplant area.

Any suitable fluid may be used for fluid 502. In various embodiments, fluid 502 may be a liquid alginate. For example, fluid 502 may include a 20 mM MOPS buffer to maintain the proper pH and prevent divalent ions (e.g., Mg, Ca, Na, etc.), 1 mM of taurine as an antioxidant and osmolyte, and 2% alginate, in one embodiment. In other embodiments, a hyaluronic acid solution may be used for fluid 502 instead of an alginate. For example, a 0.1-2.5% hyaluronic acid solution may be used for fluid 502. However, hyaluronic acid is not biodegradable like alginate and will need to be squeezed out of the transplant area using a standard surgical approach, such as applying a heavy liquid to the area (e.g., Perfluron™, etc.).

Also as shown, tissue 506 may be coated with a biodegradable material 504 that acts as a clamp/buffer around tissue 506. After implantation of tissue 506, material 504 may break down within the eye, without causing any damage to the eye. In one embodiment, material 504 may comprise an encapsulation agent such as a cured alginate. For example, the alginate solution disclosed above may be used to coat tissue 506 and sprayed with a 2% solution of a CaCl2 mist, to solidify the alginate around tissue 506.

Figure 6:
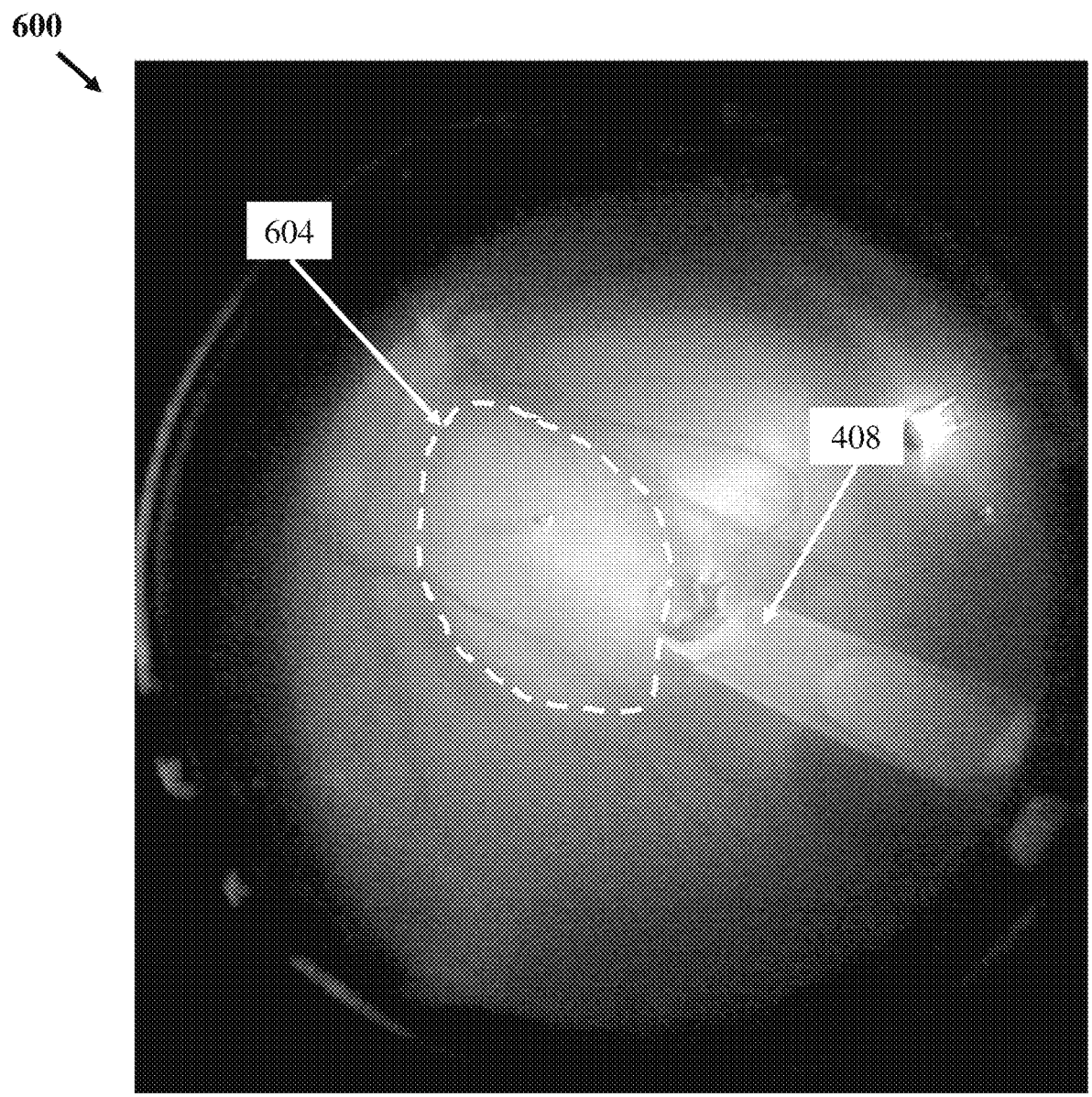
FIGS. 6-8 depict transplantation of ocular tissue into a test subject using the disclosed surgical tool.
Figure 7:
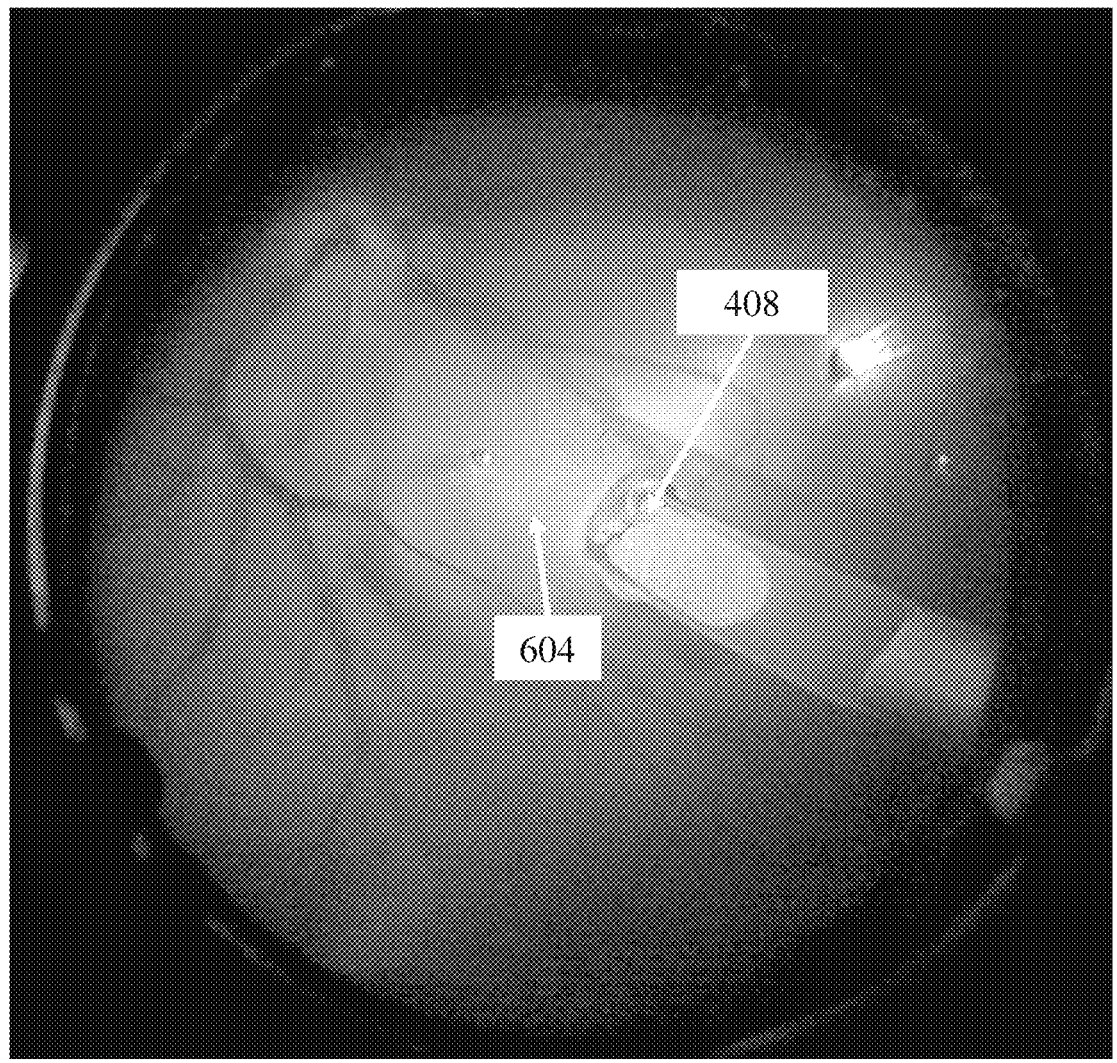
Figure 8:
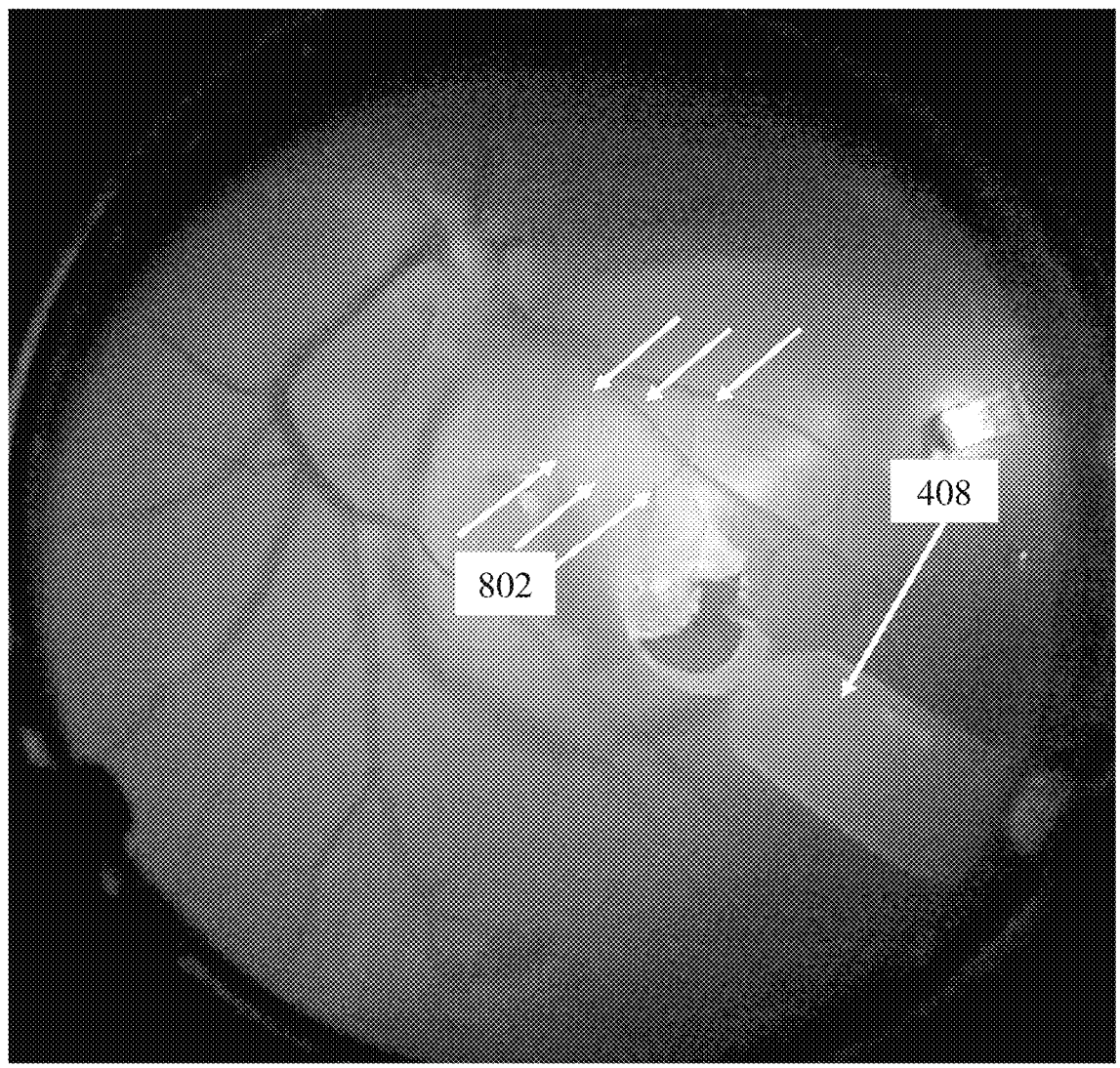

FIGS. 6-8 depict transplantation of ocular tissue into a test subject using the disclosed surgical tool. As shown in FIGS. 6-7, tip 408 is inserted into retinotomy site 602 under detachment area 604. In doing so, a sheet of tissue held in place within tip 408 by the hydraulic pressure discussed above within injector portion 112 may be positioned within the eye. Once positioned, the hydraulic pressure may be reversed, thereby providing an injection force to the tissue and driving the tissue into site 602. Tip 408 may then be withdrawn from site 602 after deposition of scaffold 802 into site 602.

Figure 9:
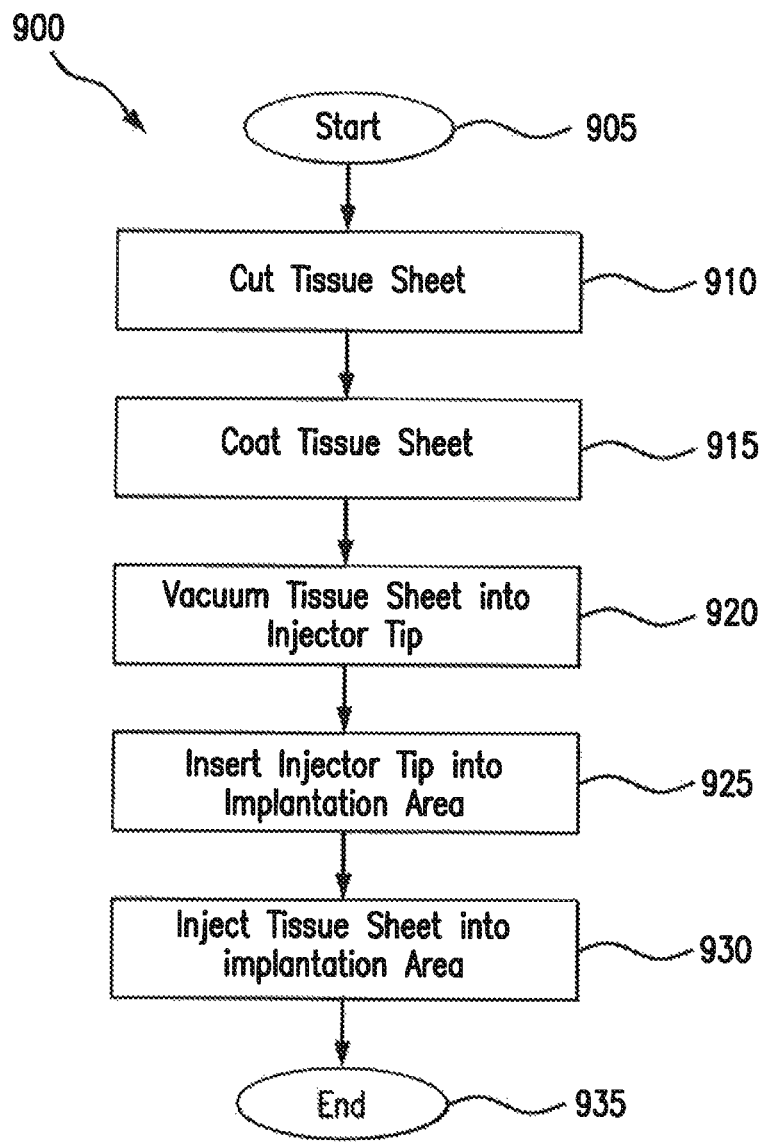
FIG. 9 is a simplified procedure for using a surgical tool to perform soft tissue transplantation.

A simplified procedure 900 is shown in FIG. 9 for using a surgical tool to perform soft tissue transplantation, according to various embodiments. Procedure 900 may start at step 905 and continue on to step 910 where a sheet of tissue is cut. For example, a monolayer RPE culture may be cut accordingly for transplantation into a patient's eye. At step 910, the cut sheet of tissue may be coated with a biodegradable material, as described in greater detail above. For example, the tissue may be coated in a cured alginate prior to transplantation. At step 920, the sheet of tissue may then be vacuumed into the tip of a surgical injector using hydraulic pressure, as detailed above. At step 925, the tip of the injector may then be inserted into the implantation area of the eye, as described in greater detail above. At step 930, the sheet of tissue may then be injected into the implantation area by applying a hydraulic pressure to the tissue held in place within the surgical injector that is opposite in direction to the vacuum pressure. Procedure 900 then ends at step 935.

According to an exemplary embodiment, the outermost diameter of a portion of the instrument that is inserted into the eye is no greater than that which can fit through an incision about 4 mm or less, and more preferably about 3 mm or less (e.g. about 2 mm or less or even about 1 mm or less). In particular, the present device and method are configured for insertion and delivery of a tissue through an incision in a human eye that is preferably about 1-3 mm. For smaller eyes such as a rat eye, the incision is generally slightly less, and is preferably no greater than about 1 mm. Preferably for a rat eye, the outer diameter of the distal portion of the device that is inserted into the eye is about 23 Ga or less, and about 19-18 Ga or less for a human eye. The size of the piece of tissue or cells that is inserted into the eye can also vary. Implants as small as about 0.8-1 mm in diameter (if circular) or length (if generally square or rectangular or irregularly shaped) and up to about 2-3 mm in diameter or length can be inserted using the described instrument. Of course, smaller and larger sized implants can also suitably be inserted (e.g. wherein the larger sized implants may be curved to a greater extent).

The present device and method are adapted, in particular, for tissue transplantation procedures in animal and human eyes, particularly in connection with the transplantation of repair tissues derived from stem cell technologies. Stem cell research is a fast developing field which allows for the production of tissues suitable for transplantation. However, there are no simple, inexpensive and familiar tools available to surgeons for delivering such tissues without causing extensive damage to the tissues and which allow for specific and accurate placement of the tissue. The present device and method address this need. In particular, the present device and method is new, inexpensive and simple to use, and is based on an instrument that is familiar to surgeons. The present device and method enables delivery of intact undamaged pieces of tissue into an animal or human eye, particularly into the subretinal space. The present device and method also allows for the control of tissue directionality when it is placed in the subretinal space, which is necessary for the transplanted tissue to be functional. Currently, there are no available instruments that provide this. The present instrument and method further enables "regular" vitreous cavity transplantation, which is very different from transplantation techniques from the outside eye (sclera-choroid). This sclera-choroid approach is more suitable for animals, but is causes enormous damage to the eye tissues rendering it unsuitable for use on humans. As such, the present device and method can be used on the human eye. Additionally, the tool design allows for handling of very fragile tissue and can be used in any surgeries where implantable tissues are too fragile for handling with mechanical means. The present instrument further allows delivery of any other flat carrier which may be loaded with medications or biological reactors delivering medications. The present instrument is not limited to retinal surgery but can be used in other surgical fields such brain surgery, skin surgery, pancreas function restoration, stem cell surgery, thyroid restoration surgery, and other similar surgeries.

The present invention also relates to kits and methods involving such ocular procedures for the precise delivery of tissues or cells in the eye, particularly the subretinal space (SRS).

All patents, publications, CAS numbers, and accession numbers mentioned in this specification are herein incorporated by reference to the same extent as if each independent patent and publication was specifically and individually indicated to be incorporated by reference.

What is claimed is:

1. A device for performing tissue transplantation within an eye comprising:
   a hollow handle portion configured to convey a fluid therein; and
   an injector portion fluidically coupled to the handle portion and defining an internal channel via which the fluid is conveyed, the injector portion comprising:
   a substantially flat shaped tip that defines an aperture connected to the internal channel of the injector portion and configured to enshroud a tissue for transplantation, wherein the tissue is held in place within the aperture when a vacuum pressure is applied to the tissue via the fluid, wherein the tissue is injected into the eye when an injection pressure that is opposite in direction to the vacuum pressure is applied to the tissue via the fluid, wherein the tip comprises opposing distal and proximal ends defining a tapered configuration wherein the proximal end couples to the handle portion of the device and the distal end having a semi-circular edge and is configured for insertion into an eye, the tip defining an aperture entirely spaced apart from its distal end such that a portion of the distal end enters an eye prior to entry of the aperture;
   an elongated portion that defines a longitudinal axis; and
   a middle portion that curves away from the longitudinal axis of the elongated portion, wherein the proximal end of tip of the injector extends from the middle portion and curves towards the longitudinal axis.

2. The device of claim 1, further comprising:
   a syringe configured to house a reservoir of the fluid, wherein the syringe is fluidically coupled to the handle portion to convey the fluid between the syringe and the handle portion.

3. The device of claim 1, wherein the handle portion and the injector portion are removably coupled.

4. The device of claim 1, wherein the fluid is a liquid alginate solution.

5. The device of claim 1, wherein the fluid is a hyaluronic acid solution.

6. The device of claim 1, wherein the tissue is coated in a cured alginate.

7. A device for performing tissue transplantation within an eye comprising:
   a hollow handle portion configured to convey a fluid therein; and
   an injector portion fluidically coupled to the handle portion and defining an internal channel via which the fluid is conveyed, the injector portion comprising:
   a substantially flat shaped tip that defines an aperture connected to the internal channel of the injector portion and configured to enshroud a tissue for transplantation, wherein the tissue is held in place within the aperture when a vacuum pressure is applied to the tissue via the fluid, and wherein the tissue is injected into the eye when an injection pressure that is opposite in direction to the vacuum pressure is applied to the tissue via the fluid, wherein the tip comprises opposing distal and proximal ends defining a tapered configuration wherein the distal end has a semi-circular edge and is configured for insertion into an eye, the tip defining an aperture entirely spaced apart from its distal end such that a portion of the distal end enters an eye prior to entry of the aperture; and
   a syringe pump or other device capable of producing vacuum and pressure coupled to a syringe and configured to regulate the vacuum and insertion pressures.

8. The device of claim 7, wherein the syringe pump is electronically controlled.

9. A method of transplanting tissue into an eye comprising:
   vacuuming a sheet of tissue into an aperture of a tip of a surgical injector tool, wherein the aperture provides a suction force to the sheet of tissue via a fluid;
   inserting the tip of the injector tool into an implantation area of the eye; and
   injecting the sheet of tissue into the implantation area by providing an injection force to the sheet of tissue, via the fluid, that is opposite to the suction force, wherein the surgical injector tool comprises:
   a substantially flat shaped tip that includes opposing distal and proximal ends defining a tapered configuration wherein the distal end has a semi-circular edge and is configured for insertion into an eye, the tip defining an aperture entirely spaced apart from its distal end such that a portion of the distal end enters an eye prior to entry of the aperture;
   an injector portion with an elongated portion that defines a longitudinal axis; and a middle portion that curves away from the longitudinal axis of the elongated portion,
   wherein the proximal end of the tip of the injector extends from the middle portion and curves towards the longitudinal axis.

10. The method as in claim 9, further comprising:
    cutting the sheet into a desired shape for implantation; and
    coating the cut sheet of tissue with a biodegradable material.

11. The method as in claim 10, wherein the biodegradable material is an alginate material cured using a calcium chloride mist.

12. The method as in claim 9, wherein the fluid is a liquid alginate solution.

13. The method as in claim 9, wherein the fluid is a hyaluronic acid solution.

14. The method as in claim 9, wherein the surgical injector tool is curved in a direction extending distally away from a handle of the surgical injector tool.

15. The method as in claim 9, further comprising:
    using a syringe to regulate the fluid such that the suction and injection forces are applied to the sheet of tissue.

16. A system for performing tissue transplantation within an eye comprising:

means for hydraulically securing a sheet of tissue to be implanted; and means for injecting the secured sheet of tissue into a transplantation area of the eye, the means for injecting having an injector portion, comprising:

a substantially flat shaped tip that includes opposing distal and proximal ends defining a tapered configuration wherein the distal end has a semi-circular edge and is configured for insertion into an eye, the tip defining an aperture entirely spaced apart from its distal end such that a portion of the distal end enters an eye prior to entry of the aperture;

an elongated portion that defines a longitudinal axis; and a middle portion that curves away from the longitudinal axis of the elongated portion, wherein the proximal end of the tip of the injector extends from the middle portion and curves towards the longitudinal axis.

17. The system of claim 16, further comprising:

means for positioning the sheet of tissue for injection into the transplantation area of the eye.

\* \* \* \* \*